United States Patent
Miyahara et al.

(10) Patent No.: US 9,192,914 B2
(45) Date of Patent: Nov. 24, 2015

(54) SILICA SPHERES AND AFFINITY CARRIER

(71) Applicant: AGC SI-TECH CO., LTD., Kitakyushu-shi (JP)

(72) Inventors: Hiroyoshi Miyahara, Kitakyushu (JP); Ryou Nakashima, Kitakyushu (JP); Kenji Higashi, Kitakyushu (JP)

(73) Assignee: AGC Si-Tech Co., Ltd., Kitakyushu-shi (JP)

( * ) Notice: Subject to any disclaimer, the term of this patent is extended or adjusted under 35 U.S.C. 154(b) by 0 days.

(21) Appl. No.: 14/262,039

(22) Filed: Apr. 25, 2014

(65) Prior Publication Data

US 2014/0235435 A1 Aug. 21, 2014

Related U.S. Application Data (63) Continuation of application No. PCT/JP2012/077788, filed on Oct. 26, 2012.

(30) Foreign Application Priority Data

Oct. 28, 2011 (JP) .................................. 2011-237204

(51) Int. Cl.

| | |
|---|---|
| *C01B 33/12* | (2006.01) |
| *B01J 20/286* | (2006.01) |
| *C01B 33/193* | (2006.01) |
| *B01D 15/38* | (2006.01) |
| *B01J 20/28* | (2006.01) |
| *B01J 20/30* | (2006.01) |
| *B01J 20/32* | (2006.01) |
| *B01J 20/10* | (2006.01) |
| *C07K 17/14* | (2006.01) |
| *C07K 1/22* | (2006.01) |

(52) U.S. Cl.
CPC ........... *B01J 20/286* (2013.01); *B01D 15/3809* (2013.01); *B01J 20/103* (2013.01); *B01J 20/28004* (2013.01); *B01J 20/28019* (2013.01); *B01J 20/28076* (2013.01); *B01J 20/28085* (2013.01); *B01J 20/3085* (2013.01); *B01J 20/3204* (2013.01); *B01J 20/3274* (2013.01); *C01B 33/193* (2013.01); *C07K 17/14* (2013.01); *C07K 1/22* (2013.01)

(58) Field of Classification Search
CPC . C01P 2004/61; C01P 2004/32; C01B 33/12; C01B 33/152
USPC .................................................. 423/335, 338
See application file for complete search history.

(56) References Cited

U.S. PATENT DOCUMENTS 5,693,223 A * 12/1997 Yamada et al. ............. 210/198.2
8,357,628 B2 * 1/2013 Wei et al. ..................... 502/400

FOREIGN PATENT DOCUMENTS

| CN | 1787874 A | 6/2006 |
|---|---|---|
| JP | 7-196310 | 8/1995 |
| JP | 7-291754 | 11/1995 |
| JP | 2006-225226 | 8/2006 |
| JP | 2007-238426 | 9/2007 |
| JP | 2008-120633 | 5/2008 |
| JP | 2009-31277 | 2/2009 |
| JP | 2011-1336 | 1/2011 |

OTHER PUBLICATIONS

International Search Report issued Feb. 5, 2013 in PCT/JP2012/077788 filed Oct. 28, 2011.

* cited by examiner

*Primary Examiner* — Matthew E Hoban
*Assistant Examiner* — James Fiorito
(74) *Attorney, Agent, or Firm* — Oblon, McClelland, Maier & Neustadt, L.L.P.

(57) ABSTRACT

To provide an affinity carrier with a low pressure loss and a large binding capacity even when the linear flow rate of a solution to be made to pass therethrough is high.

Silica spheres, which satisfy the following conditions:
(a) the average particle size is from 30 μm to 40 μm as measured by a laser light scattering method; (b) the ratio (D10/D90) of the particle size (D10) of smaller 10% cumulative volume to the particle size (D90) of 90% cumulative volume in a particle size distribution as measured by a Coulter counter method, is at most 1.50; and (c) the average pore size is from 85 nm to 115 nm and the pore volume is at least 1.5 mL/g, as measured by a mercury intrusion technique.

13 Claims, 2 Drawing Sheets

BB: Example 2
CC: Comparative Example 4
DD: Comparative Example 5
EE: Comparative Example 6
FF: Comparative Example 7
GG: Comparative Example 8

SILICA SPHERES AND AFFINITY CARRIER

TECHNICAL FIELD

The present invention relates to silica spheres and an affinity carrier.

BACKGROUND ART

In recent years, high precision purification or removal of a specific protein is emphasized in medical and pharmaceutical fields. For example, in order to purify a chemical having a specific function, it is necessary to purify a specific protein highly precisely.

In affinity chromatography, protein A having a specific binding property as a ligand is widely used. Protein A is a protein originating from gram-positive Eubacteria *Staphylococcus*, specifically binds to the Fc regions of IgGs from various animals, and is widely used to purify IgG. A technique has been widely known in which the protein A is immobilize to an insoluble carrier, and by affinity chromatography using the insoluble carrier, IgG is specifically isolated and purified.

In an affinity carrier employed for affinity chromatography, usually, a structure called linker is interposed between the insoluble carrier and the ligand, and one end of the linker is bonded to the carrier and the other end of the linker is bonded to the ligand, to immobilize the ligand to the insoluble carrier (Patent Document 1).

Patent Document 2 proposes chromatography with an improved dynamic capacity and with a higher flow rate in a shorter residence time, by a solid phase carrier suitable for application to affinity chromatography, containing silica particles having pore sizes larger than 630 Å and smaller than 1,000 Å and having an average particle size larger than 55 μm and smaller than 70 μm. However, in Patent Document 2, the pressure loss tends to increase if the average silica particle size is decreased so as to increase the amount of the silica particles packed, and if the pressure loss is high, the upper limit of the linear flow rate may be restricted.

PRIOR ART DOCUMENTS

Patent Documents

Patent Document 1: JP-A-2011-1336
Patent Document 2: JP-A-2009-31277

DISCLOSURE OF INVENTION

Technical Problem

The object of the present invention is to provide an affinity carrier with a low pressure loss and a large binding capacity even when the linear flow rate of a solution to be made to pass therethrough is high.

Solution to Problem

The present invention provides silica spheres, which satisfy the following conditions: (a) the average particle size is from 30 μm to 40 μm as measured by a laser light scattering method; (b) the ratio (D90/D10) of the particle size (D90) of 90% cumulative volume to the particle size (D10) of smaller 10% cumulative volume in a particle size distribution as measured by a Coulter counter method, is at most 1.50; and (c) the average pore size is from 85 nm to 115 nm and the pore volume is at least 1.5 mL/g, as measured by a mercury intrusion technique.

The present invention further provides an affinity carrier comprising the silica spheres and having a ligand immobilized to the silica spheres.

Advantageous Effects of Invention

According to the present invention, it is possible to provide an affinity carrier with a low pressure loss and a large binding capacity even when the linear flow rate of a solution to be made to pass therethrough is high.

DESCRIPTION OF EMBODIMENTS

Now, the present invention will be described. However, the present invention is by no means restricted to such specific embodiments.

According to one embodiment of the present invention, silica spheres satisfy the following conditions: (a) the average particle size is from 30 μm to 40 μm as measured by a laser light scattering method; (b) the ratio (D90/D10) of the particle size (D90) of 90% cumulative volume to the particle size (D10) of smaller 10% cumulative volume in a particle size distribution as measured by a Coulter counter method, is at most 1.50; and (c) the average pore size is from 85 nm to 115 nm and the pore volume is at least 1.5 mL/g, as measured by a mercury intrusion technique. By such silica spheres, it is possible to provide an affinity carrier with a low pressure loss and a large binding capacity even when the linear flow rate of a solution to be made to pass therethrough is high.

By comparison of columns having the same volume, it is considered that when silica spheres having a smaller average particle size are used, the effective volume per silica spheres tends to increase, and thus the binding capacity which is the capability to bind antibody molecules (such as a protein) per carrier is larger, however, the pressure loss tends to be high. According to the present invention, by using silica spheres having a specific small average particle size and having a low proportion of the above ratio (D90/D10), i.e. silica spheres having a sharp particle size distribution, an affinity carrier with a low pressure loss and a large capacity can be provided.

On the other hand, if agarose or a resin filler such as polymethacrylate is used as a base material of the affinity carrier, due to its flexibility, the pressure loss tends to be high, and the pressure loss tends to be high particularly at a high linear flow rate. Further, if ground glass or ceramic pieces are used as the base material of the affinity carrier, due to its shape, the pressure loss tends to be high.

Further, by the silica spheres according to this embodiment, since the average particle size is small and the proportion of (D90/D10) is low, the average pore size is within an appropriate range, and the pore volume is large, it is possible to provide an affinity carrier having a large binding capacity.

Usually, the binding capacity is considered to decrease as the linear flow rate is higher, however, by the silica spheres according to this embodiment, a large binding capacity can be achieved even at a high linear flow rate. That is, the silica spheres according to this embodiment are excellent in the dynamic binding capacity. Further, since the silica spheres according to this embodiment provide a low pressure loss even at a high linear flow rate, the dynamic binding capacity can be made larger.

Here, the binding capacity includes the static binding capacity (SBC) and the dynamic binding capacity (DBC). The static binding capacity represents the upper limit amount of the antibody molecules which the carrier can adsorb, and the dynamic binding capacity represents the degree how the antibody molecules can be recovered in a state where a solution containing the antibody molecules are made to pass through the column. A carrier having a large dynamic binding capacity can efficiently adsorb antibody molecules even at a high linear flow rate, and the antibody molecules can be purified in a short time with such a carrier.

Preferably, by the silica spheres according to this embodiment, it is possible to provide an affinity carrier having a dynamic binding capacity for antibody molecules of at least 50 mg/mL-bed, more preferably at least 60 mg/mL-bed, and having a pressure loss of at most 5 bar, more preferably at most 3 bar, at a high flow rate (corresponding to 1,200 cm/hr for a 20 cm column) for a residence time of one minute.

The shape of the silica spheres is not particularly limited so long as it is spherical, including roundly spherical and elliptic, and from the viewpoint of packing into a column and suppression of the pressure loss at the time of use, the shape is preferably close to roundly spherical.

The average particle size of the silica spheres is from 30 μm to 40 μm, preferably from 32 μm to 38 μm, further preferably from 33 μm to 37 μm. By the average particle size being at least 30 μm, the increase in the pressure loss can be prevented while maintaining a large binding capacity. Further, by the average particle size being at most 40 μm, the effective volume per particle can be increased, and the binding capacity can be made large. Here, the average particle size of the silica spheres is the average particle size as calculated as volume as measured by a laser light scattering method. Specifically, the average particle size of the silica spheres can be measured by e.g. "LA-950V2" manufactured by Horiba, Ltd.

The ratio (D90/D10) of the particle size (D90) of 90% cumulative volume to the particle size (D10) of smaller 10% cumulative volume in a particle size distribution (hereinafter sometimes referred to as "uniformity coefficient"), as measured by a Coulter counter method, is at most 1.50, preferably at most 1.40, further preferably at most 1.35. By the uniformity coefficient being at most 1.50, the increase in the pressure loss can be prevented even when the silica spheres have a small average particle size. Further, the closer to 1 the uniformity coefficient is, the more uniform the particle size distribution is, such being favorable.

Here, the uniformity coefficient of the silica spheres is measured by a Coulter counter method. D10 represents the particle size of the 10% cumulative volume when the volumes of the particle sizes are cumulated from the small particle size side in a particle size distribution measured by a Coulter counter method, and D90 represents the particle size of the 90% cumulative volume measured in the same manner. The uniformity coefficient (D90/D10), which is the ratio of such particle sizes, can be obtained from D10 and D90 obtained by measurement of the silica spheres e.g. by "Multisizer III" manufactured by Beckman Coulter, Inc.

The average pore size of the silica spheres, as measured by a mercury intrusion technique, is from 85 nm to 115 nm, preferably from 90 nm to 110 nm, more preferably from 95 nm to 105 nm. By the average pore size being at least 85 nm, a carrier having an improved capability to adsorb antibody molecules and having a large capacity can be provided. Further, by the average particle size being at most 115 nm, a decrease in the strength of the silica spheres can be prevented while maintaining a large amount of adsorption of antibody molecules.

The pore volume of the silica spheres, as measured by a mercury intrusion technique, is at least 1.5 mL/g, preferably at least 1.55 mL/g, more preferably at least 1.6 mL/g. By the pore volume being at least 1.5 mL/g, a carrier having an improved capability to adsorb antibody molecules and having a large capacity can be provided. Further, the pore volume is preferably at most 1.8 mL/g from the viewpoint of the strength of the silica spheres.

The specific surface area of the silica spheres, as measured by a mercury intrusion technique, is preferably from 55 $m^2/g$ to 75 $m^2/g$, more preferably from 60 $m^2/g$ to 75 $m^2/g$. The specific surface area can be optimized to fit with the purpose of use together with the average pore size and the pore volume. When the specific surface area is large, the capability to adsorb antibody molecules will improve, such being preferred, however, if it is large, the strength of the silica spheres tends to decrease, and accordingly the specific surface area is preferably set within the above range.

The pore physical properties by a mercury intrusion technique can be measured e.g. by "Mercury Porosimeter Autopore IV9510" manufactured by Shimadzu Corporation.

The above silica spheres can be used for an affinity carrier. The affinity carrier is one comprising the above silica spheres as a base material and having a ligand immobilized to the silica spheres. The ligand may, for example, be protein A, protein G, concanavalin A, antigens or antibodies.

In a case where protein A is used as the ligand, the affinity carrier, which comprises the above silica spheres as a base material, has an amount of protein A immobilized of at least 10.0 g/L-bed, more preferably at least 11.0 g/L-bed, further preferably at least 11.5 g/L-bed.

To measure the amount of protein A immobilized, the carrier having protein A immobilized thereto is dried, and the carrier is subjected to elemental analysis.

Such an affinity carrier can have a dynamic binding capacity for antibody molecules of at least 50 mg/mL-bed, further at least 60 mg/mL-bed, and a pressure loss of at most 5 bar, further at most 3 bar, at a high linear flow rate (corresponding to 1,200 cm/hr for a 20 cm column) for a residence time of 1 minute. Further, such an affinity carrier has a static binding capacity of at least 80 mg/mL-bed, further at least 85 mg/mL-bed.

To measure the pressure loss, the affinity carrier is packed in a column, this column is set to a chromatography apparatus, and distilled water is made to pass through the column at various linear flow rates to determine the operating pressure. Then, an empty column is set to a chromatography apparatus, and distilled water is made to pass through the empty column at various linear flow rates similarly to determine the operating pressure, which is subtracted from the operating pressure of the column in which the affinity carrier is packed, to obtained the pressure loss.

The dynamic binding capacity is obtained in such a manner that the affinity carrier is packed in a column, this column is set to a chromatography apparatus, a sample solution containing antibody molecules is made to pass through the column at a predetermined linear flow rate, the absorbance of the eluate is measured, and from the mass of the antibody molecules added when the breakthrough of a predetermined ratio (for example, 10%) of the absorbance of the added sample solution is measured, the dynamic binding capacity can be obtained. The absorbance may be measured e.g. by "UV-1800" manufactured by Shimadzu Corporation.

Further, to obtain the static binding capacity, a solution containing antibody molecules at a predetermined concentration is added to the affinity carrier and properly mixed and stirred, followed by centrifugal separation, and the amount of antibody molecules in the supernatant fluid is measured by absorbance measurement, and the static binding capacity can be obtained by a Langmuir plot method. The absorbance may be measured e.g. by "UV-1800" manufactured by Shimadzu Corporation.

Now, the method for producing the silica spheres and the affinity carrier is described below. Now, as an example, a method for preparing silica spheres having the above physical properties and immobilizing protein A to the silica spheres will be described.

The method for producing silica spheres having the above physical properties is not particularly limited, and as an example, a dispersed phase containing a silica precursor and a continuous phase are emulsified, and the obtained emulsion is gelated to obtain silica spheres. As the case requires, a treatment to increase the average pore size and the pore volume of the silica spheres may properly be carried out.

As the emulsification step, preferred is a method of supplying a dispersed phase containing a silica precursor to a continuous phase by means of micropores or a porous membrane to prepare an emulsion. By such a method, an emulsion having a uniform droplet size can be prepared and as a result, silica spheres having an uniform particle size having a uniformity coefficient of at most 1.5 can be obtained. As such an emulsification step, as an example, a micromixer method or a membrane emulsification method may be employed.

Now, preparation of a W/O emulsion using an aqueous liquid containing a silica precursor as the dispersed phase containing a silica precursor and an organic liquid as the continuous phase, will be described as an example. Further, it is also possible to prepare an O/W emulsion using an organic liquid as the dispersed phase containing a silica precursor and an aqueous liquid as the continuous phase.

As the aqueous liquid containing a silica precursor, any liquid may be applicable so long as precipitates can be formed by solidification. Specifically, an aqueous solution having a water-soluble silica dispersed therein, or an aqueous dispersion having a solid silica such as silica sol obtained by hydrolysis of an organic silicon compound or commercially available silica sol dispersed therein, may be mentioned. Particularly, an aqueous solution of an alkali metal silicate is preferably used. The alkali metal may, for example, be lithium, sodium, potassium or rubidium, and among them, in view of availability and economical efficiency, sodium is most preferred. The proportion of silicic acid to sodium is, by $SiO_2/Na_2O$ (molar ratio), preferably from 2.0 to 3.8, more preferably from 2.0 to 3.5. Further, the concentration of the alkali metal silicate aqueous solution is, as the $SiO_2$ concentration, preferably from 5 to 30 mass %, more preferably from 5 to 25 mass %.

The organic liquid is not particularly limited, and a liquid insoluble in an aqueous liquid may be used. For example, one of the following or two or more in combination may be used.

An aliphatic hydrocarbon such as n-hexane, isohexane, n-heptane, isoheptane, n-octene, isooctene, nonane or decane, an alicyclic hydrocarbon such as cyclopentane, cyclohexane or cyclohexene, an aromatic hydrocarbon such as benzene, toluene, xylene, ethylbenzene, propylbenzene, cumene, mesitylene, tetralin or styrene, an ether such as propyl ether or isopropyl ether, and an ester such as ethyl acetate, n-propyl acetate, isopropyl acetate, n-butyl acetate, isobutyl acetate, n-amyl acetate, isoamyl acetate, butyl lactate, methyl propionate, ethyl propionate, butyl propionate, methyl butyrate, ethyl butyrate or butyl butyrate.

The organic liquid is preferably a $C_{9-12}$ saturated hydrocarbon, and is selected comprehensively considering the operation property, the safety against fire, separation property of the solidified particles and the organic liquid, the shape of the silica spheres, the solubility of the organic liquid in water, etc. The $C_{9-12}$ saturated hydrocarbons may be used alone or in combination of two or more. Further, the $C_{9-12}$ saturated hydrocarbon may be a linear hydrocarbon or a hydrocarbon having side chains so long as it is chemically stable.

The $C_{9-12}$ saturated hydrocarbon preferably has a flash point of from 20 to 80° C., more preferably from 30 to 60° C. If a saturated hydrocarbon having a flash point less than 20° C. is used as the organic liquid, due to too low flash point, countermeasure against fire and for work environment is necessary. Further, one having a flash point higher than 80° C. is less likely to be volatile, whereby the amount of the hydrocarbon attached to the obtainable silica spheres may be large.

In this embodiment, after the emulsion is solidified, the silica spheres and the organic liquid are usually separated by solid-liquid separation. The organic liquid attached to or adsorbed in the silica spheres after separation is preferably separated e.g. by filtration, washing or drying.

In this embodiment, for formation of the W/O emulsion, a surfactant is preferably used. As the surfactant, for example, one of the following or two or more in combination may be used.

A sorbitan fatty acid ester surfactant such as sorbitan monostearate, sorbitan monolaurate, sorbitan monopalmitate, sorbitan monostearate, sorbitan tristearate, sorbitan monooleate or sorbitan trioleate;

a polyoxyethylenesorbitan fatty acid ester surfactant such as polyoxyethylenesorbitan monolaurate, polyoxyethylenesorbitan monopalmitate, polyoxyethylenesorbitan monostearate, polyoxyethylenesorbitan tristearate, polyoxyethylenesorbitan monooleate or polyoxyethylenesorbitan stearate;

a polyoxyethylene higher alcohol ether surfactant such as polyoxyethylenelauryl ether, polyoxyethylenecetyl ether, polyoxyethylenestearyl ether, polyoxyethyleneoleyl ether, polyoxyethyleneoctylphenol ether or polyoxyethylenenonylphenol ether;

a polyoxyethylene fatty acid ester surfactant such as polyoxyethyleneglycol monolaurate, polyoxyethyleneglycol monostearate or polyoxyethyleneglycol monooleate; and a glycerin fatty acid ester surfactant such as monoglyceride stearate or monoglyceride oleate.

Further, a polyoxyethylenesorbitol fatty acid ester surfactant, a sucrose fatty acid ester surfactant or a polyglycerin fatty acid ester polyoxyethylene hydrogenated castor oil surfactant may, for example, be used.

The amount of use of the surfactant varies depending upon the conditions such as the type of the surfactant, HLB (hydrophile-lipophile balance) which is an index of the hydrophilicity or the hydrophobicity of the surfactant, and the particle size of the desired silica spheres, and is preferably from 500 to 20,000 ppm, more preferably from 1,000 to 10,000 ppm in the organic liquid. If it is less than 500 ppm, the emulsion tends to be unstable. Further, if it exceeds 20,000 ppm, the amount of the surfactant attached to the silica spheres as a product tends to be large, such being unfavorable.

The volume ratio of the aqueous liquid containing a silica precursor to the organic liquid at room temperature (from 20 to 23° C.) is preferably from about 1 to about 100 as the W/O ratio in the obtainable emulsion.

As an embodiment of the emulsification step, the aqueous liquid containing a silica precursor is extruded through micropores into the organic liquid flowing in a laminar flow, whereby an emulsion in which the organic liquid is the continuous phase and in the continuous phase, droplets of the aqueous liquid containing a silica precursor are present as the dispersed phase, i.e. a W/O emulsion can be formed (for example, by the method as disclosed in Japanese Patent No. 4,193,626).

In this embodiment, by the flow rate of the organic liquid being from 0.001 to 5 m/s, emulsion droplets with a narrow droplet size distribution are formed, and the droplet size distribution of the obtainable silica spheres can also be made narrow. The flow rate of the organic liquid is more preferably from 0.1 to 4 m/s.

The Reynolds number of the organic liquid flowing in the flow path is preferably at most 2,100. Here, the Reynolds number in a case where the cross section of the flow path is circular is calculated in accordance with the Formula 2, and the inner diameter D of the flow path is the minimum diameter in the cross section of the flow path. Here, D is the inner diameter of the flow path (m), u is the average flow rate (m/s), $\rho$ is the liquid density (kg/m$^3$), and $\mu$ is the liquid viscosity (Pa·s).

$$\text{Reynolds number}(-)=D\cdot u\cdot\tau/\mu \qquad \text{Formula 2}$$

Further, the Reynolds number in a case where the cross section of the flow path is not circular is calculated in accordance with the Formula 3. Here, r is the flow path hydraulic radius (m)=the cross section (m$^2$) of the flow path/the perimeter (m) of the cross section of the flow path in contact with the fluid, and u, $\rho$ and $\mu$ are as defined in the Formula 2.

$$\text{Reynolds number}(-)=4\times r\cdot u\cdot\rho/\mu \qquad \text{Formula 3}$$

In a case where the Reynolds number is at most 2,100, the flow of the organic liquid is in a laminar flow state, and the flow of the organic liquid is stable. As a result, a W/O emulsion in which the aqueous liquid containing a silica precursor supplied through the micropores always has a constant droplet size is prepared, whereby silica spheres having a substantially uniform droplet size are likely to be produced. On the other hand, in a case where the Reynolds number exceeds 2,100, the flow of the organic liquid is in a turbulent flow state, a W/O emulsion in which the droplet sizes are non-uniform as in the case of the conventional emulsion, will be obtained, and as a result, the particle sizes of the silica spheres are also non-uniform in some cases. The shape of the flow path of the organic liquid is not particularly limited.

Figure 1:
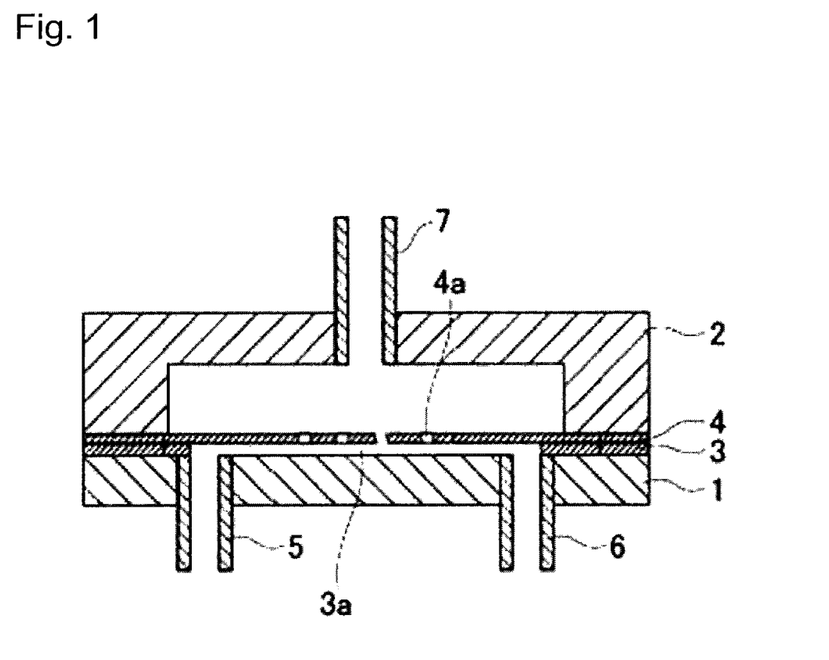
FIG. 1 is a cross-sectional view schematically illustrating an emulsification apparatus according to one embodiment of the present invention.

FIG. 1 is a cross-sectional view schematically illustrating an example of an emulsification apparatus to carry out the emulsification step. In FIG. 1, reference symbols 1 and 2 represent a member made of an acrylic resin, 3 a stainless steel plate forming a flow path 3a by etching treatment, and 4 a stainless steel plate having its surface subjected to hydrophobicity treatment, having a plurality of micropores 4a formed thereon. Further, the organic liquid is supplied from a continuous phase supply port 5 and flows in the flow path 3a in a laminar flow state so that it is discharged from a continuous phase discharge port 6, and the aqueous liquid containing a silica precursor is supplied from a dispersed phase supply port 7 and is injected into the organic liquid via the micropores 4a. As the flow path 3a formed by the stainless steel plate 3, a plurality of flow paths 3a may be formed along the direction of flow of the liquid.

In the example shown in FIG. 1, the aqueous liquid is injected through the micropores pierced in the direction of the thickness of a partition wall which compartmentalizes the flow path of the organic liquid, whereby the aqueous liquid and the organic liquid are mixed at right angles, and accordingly an effect to cut off the emulsion droplets by the flow of the organic liquid is likely to be obtained, and silica spheres having small particle sizes are likely to be obtained stably.

Further, it is preferred that a plurality of micropores are formed in one flow path. In such a case, it is preferred that a plurality of micropores are formed at an interval of at least ½ of the diameter of a circle which is circumscribed about the cross-sectional shape of each micropore on the flow path of the organic liquid. The interval is more preferably at least the diameter of a circle which is circumscribed about the cross-sectional shape of each micropore. If the micropores are provided only at an interval shorter than ½ of the diameter of a circumscribed circle, droplets of the emulsion may be united and as a result, the droplet sizes may be non-uniform. However, the micropores are preferably disposed as close as possible within a range where the droplets are not united, thus improving the productivity.

In this embodiment, the material of the partition wall in which the micropores are provided, is preferably one resistant to the aqueous liquid containing a silica precursor and the organic liquid. A material composed mainly of a metal is preferred in view of excellent processability and strength, and in addition, a material composed mainly of a resin may also be suitably used. As the resin, preferably at least one member selected from polyphenylene sulfide, polyether ether ketone, polyimide, polyamideimide, aromatic polyester and a fluororesin is preferably used, whereby excellent processability and dimensional stability will be obtained.

Further, the material of the partition wall in which the micropores are provided preferably has an affinity to the continuous phase (in this case, an affinity to the organic liquid). Accordingly, in the case of a metal material, it is preferred to apply a treatment to make it have an affinity to the organic liquid by a method of baking an oil, by a reaction with a hydrophobizing agent, coating with a hydrophobic polymer, or the like. This is to promote separation of the aqueous liquid containing a silica precursor from the partition wall after it passed through the micropores. It becomes evident by observation with a high speed camera that in a case where the partition wall is hydrophilic, the aqueous liquid will flow along the partition wall after it passed through the micropores, whereby an emulsion with large particle sizes is likely to form.

In another embodiment of the emulsification step, a porous membrane may be used instead of the micropores. By supplying the aqueous liquid containing a silica precursor to the organic liquid via a porous membrane, an emulsion having a uniform droplet size can be prepared in the same manner as in the case of using the micropores. The porous membrane preferably has a surface having a repulsion for the dispersed phase (in such a case, being hydrophobic), whereby the aqueous liquid containing a silica precursor is formed into uniform droplets, which are dispersed in the organic liquid.

Examples of the porous membrane include porous glass, a filter made of a high molecular material, and a metal sintered filter.

As a step of adding a gelling agent to the emulsion to obtain silica spheres, a method of producing one silica sphere particle from one droplet of the dispersed phase of the emulsion may be mentioned.

By gelating the emulsion, the spherical dispersed droplets of the aqueous solution are gelated while the spherical shape is maintained, and spherical silica hydrogel is obtained. For gelation, it is preferred to introduce a gelling agent to the emulsion. As the gelling agent, an acid such as an inorganic acid or an organic acid is used, and particularly an inorganic acid such as sulfuric acid, hydrochloric acid, nitric acid or carbonic acid is preferred. In view of the operation property, etc., the most simple and preferred is a method of using carbon dioxide gas. As the carbon dioxide gas, pure carbon dioxide gas at a concentration of 100% may be introduced, or carbon dioxide gas diluted with the air or an inert gas may be introduced. The time required for gelation is usually preferably from 4 to 30 minutes, and the temperature at the time of gelation is preferably from 5 to 30° C.

After completion of gelation, it is preferred that the reaction system is left at rest to separate the reaction mixture into two phases of the organic liquid phase and the aqueous phase containing the silica hydrogel thereby to separate the silica gel. In a case where a saturated hydrocarbon is used as the organic liquid, the reaction mixture is separated into the organic liquid phase as an upper layer and the aqueous liquid phase containing the silica hydrogel as a lower layer, and the two phases are separated by a known means.

To the aqueous slurry of the silica hydrogel, an acid such as sulfuric acid is added as the case requires to adjust the pH to from about 1 to about 5 to complete gelation, and the aqueous slurry is subjected to filtration and washed with water to obtain silica hydrogel, which is dried at a temperature of from about 100 to about 150° C. for from about 1 to 30 hours to obtain silica spheres.

Further, in a case where an alkali silicate aqueous solution is used as the aqueous liquid containing a silica precursor and an acid is used as the gelling agent, an alkali metal salt (for example, sodium carbonate when the gelling agent is carbonic acid) is formed as a byproduct, and to prevent this salt from being included in the silica spheres, the silica hydrogel (wet cake) after filtration is preferably sufficiently washed with water. In some cases, water is again added to the wet cake after washing with water to obtain a slurry, which is subjected to filtration and washed with water again. On that occasion, as the case requires, an operation of adjusting the pH of the slurry to about 1 to about 5 and aging it again may be carried out.

The silica spheres obtained by the above emulsification step and gelling step (hereinafter sometimes referred to as "silica spheres after emulsification") have a uniform particle size, and by properly adjusting the emulsification and gelling conditions, it is possible to provide silica spheres having an average particle size, a uniformity coefficient (D90/D10), an average pore size and a pore volume within the above ranges.

The silica spheres obtained as above may further be subjected to another step to increase the average pore size and the pore volume, after the emulsification step and the gelling step, as the case requires.

For example, the average pore size of the silica spheres can be made large by any of a method of dipping the silica spheres after emulsification in phosphoric acid of from 2 to 50%, followed by heat treatment at from 100 to 700° C. (a phosphoric acid dipping/heat treatment method, for example, the method disclosed in JP-A-3-23211), a method of hydrothermal treatment at from 270 to 350° C. (a hydrothermal treatment method, for example, the method disclosed in JP-B-61-20487), and a method of filling the pores in the silica gel with an aqueous solution of an inorganic salt such as NaCl, drying the silica gel and firing it at from 350 to 1,500° C. (an inorganic salt filling/firing method, for example, the method as disclosed in JP-A-47-5817).

Further, the average pore size and the pore volume of the silica spheres after emulsification or silica spheres having pore sizes further increased after emulsification can be increased while the uniformity coefficient is maintained, by bringing them into contact with an alkaline aqueous solution or a fluorine aqueous solution (for example, the method disclosed in JP-A-2007-238426 may be employed).

In the treatment with an alkaline aqueous solution, as the alkali, a strong alkali such as an alkali metal hydroxide such as sodium hydroxide, potassium hydroxide, rubidium hydroxide or cesium hydroxide, or an alkaline earth metal hydroxide such as magnesium hydroxide, calcium hydroxide, strontium hydroxide or barium hydroxide may be used. Preferred is sodium hydroxide and/or potassium hydroxide.

The mass ratio (the mass of alkali (OH)/the mass of silica gel raw material) of the alkali to be used to the silica gel spheres is from 0.02/1 to 0.2/1, preferably at a level of from 0.05/1 to 0.15/1. If the proportion of the alkali is less than the above, the reaction to adjust the pore physical properties of the silica gel raw material may not sufficiently be carried out, and if the proportion exceeds the above, it tends to be difficult to adjust the pore physical properties while controlling them.

The concentration of the alkaline aqueous solution is from 0.1 to 40 mass %, preferably from 0.5 to 30 mass %, further preferably from 1 to 20 mass %. If the concentration is less than the above, no sufficient effect of the alkali to improve the pore physical properties of the silica gel raw material will be obtained, and if the concentration exceeds the above, the reaction will proceed too much, whereby it tends to be difficult to control the pore physical properties. The slurry concentration of the silica gel raw material in the alkaline aqueous solution is, for example, from 1 to 60 mass %, preferably from 2 to 50 mass %, further preferably from 3 to 40 mass %.

The reaction temperature is from 5 to 100° C., preferably from 10 to 80° C., further preferably at a level of from 20 to 50° C. Further, the reaction may be carried out at room temperature without heating or cooling.

The treatment time (reaction time) may vary depending upon factors such as the concentration of the alkaline aqueous solution, the reaction temperature, the ratio of the mass of the alkali to the mass of the silica gel raw material and the slurry concentration, and is usually from 1 minute to 50 hours, preferably from 10 minutes to 40 hours, further preferably from 30 minutes to 30 hours, most preferably at a level of from 1 to 24 hours.

The slurry after completion of the treatment step is subjected to solid-liquid separation by filtration or centrifugal separation, the resulting cake of the silica gel separated is again dispersed in water in a stirring bath, an appropriate acid such as sulfuric acid, hydrochloric acid or nitric acid is added to adjust the pH to be from about 1 to about 3, and the resulting mixture is stirred in a slurry state for from 0.1 to 2 hours to sufficiently wash away the alkali. As the case requires, the slurry is further subjected to filtration, washed and dried to obtain silica spheres having pore physical properties adjusted.

Instead of the above alkaline aqueous solution, a hydrogen fluoride aqueous solution may be used. In a case where a hydrogen fluoride aqueous solution is used, the same treatment may be carried out as in the case of using the alkaline aqueous solution.

The mass ratio of hydrogen fluoride to be used to the silica gel raw material (the mass of hydrogen fluoride/the mass of silica gel raw material) is from 0.1/1 to 1.8/1, preferably at a level of from 0.2/1 to 1.6/1. The concentration of the hydrogen fluoride aqueous solution is from 0.01 to 20 mass %, preferably from 0.5 to 15 mass %, further preferably from 1 to 10 mass %. When the concentration of the hydrogen fluoride aqueous solution is within the above range, the pore physical properties can be appropriately controlled.

As a step of immobilizing protein A to the silica spheres, a structure called a linker is interposed between each silica sphere and a ligand, one end of the linker is bonded to each silica sphere and the other end of the linker is bonded to the ligand, whereby the ligand can be immobilized to the silica spheres.

Now, a method of reacting silica spheres with an epoxy group-containing compound and further with protein A will be described as an example.

By reacting the silica spheres with an epoxy group-containing compound, the epoxy group-containing compound is modified to the surface of the silica spheres to form a linker. The linker has an epoxy group at its terminal.

The epoxy group-containing compound is preferably a silane coupling agent having an epoxy group. The epoxy group-containing silane coupling agent may, for example, be γ-glycidoxypropyl trimethoxysilane, γ-glycidoxypropyl methyldiethoxysilane or β-(3,4-epoxycyclohexyl)ethyl trimethoxysilane.

The method of reacting the silica spheres with the epoxy group-containing compound is not particularly limited, and for example, a method of heating the silica spheres and the epoxy group-containing compound in a solvent may be employed. The reaction temperature may, for example, be at a level of from 30 to 400° C., and is preferably from 100 to 300° C. The reaction time may, for example, be at a level of from 0.5 to 40 hours, and is preferably from 3 to 20 hours.

The solvent is not particularly limited so long as it will not react with the epoxy group-containing compound and is stable at the reaction temperature. From the viewpoint of the solubility of the epoxy group-containing compound, the boiling point and affinity with another solvent (i.e. removability at the time of washing), usually, benzene, toluene, xylene, octane, isooctane, tetrachloroethylene, chlorobenzene or bromobenzene may, for example, be used. Further, the reaction operation may be carried out under reflux of the solvent.

The amount of the epoxy group-containing compound modified is usually preferably larger, that is, an amount sufficient to densely cover the entire surface of the silica spheres, with a view to improving the alkali resistance of the silica spheres. Specifically, the reaction is preferably conducted so that the amount of the epoxy group-containing compound per 1 g of the silica spheres (the amount obtained by dividing the amount of the epoxy group-containing compound modified by the mass of the silica spheres) is at least 220 μmol/g. The amount of the epoxy group-containing compound modified is more preferably from 220 to 320 μmol/g, particularly preferably from 240 to 300 μmol/g.

Here, the amount of the epoxy group-containing compound modified is obtained based on a known method. For example, the amount of the epoxy group-containing compound modified can be calculated from the amount of carbon contained in one molecule of the epoxy group-containing compound based on the carbon content of the silica gel after the epoxy group-containing compound is modified, measured by an elemental analysis method, and the mass of the silica spheres.

In the reaction system of the silica spheres with the epoxy group-containing compound, an amine compound such as triethylamine, pyridine or diisopropylethylamine may further be mixed, whereby the reaction of the silica spheres with the epoxy group-containing compound will be promoted by the catalytic activity of the amine.

Then, protein A is immobilized to the silica spheres having a linker introduced. As the protein A, one having a lysine amino group may be used. Particularly, recombinant protein A is preferably used.

As a method of bonding the ligand to the linker structure of the silica spheres, although not limited thereto, the silica spheres and a solution containing the protein A are mixed, and the reaction is carried out in a proper solvent optionally using a catalyst, a reaction reagent or the like. In the reaction of the linker structure with the ligand, for example, the reaction temperature is from 20 to 30° C., and the reaction time is from 1 to 24 hours. The pH in the reaction system is preferably from 8 to 9.5, and may be adjusted by a buffer solution.

The amount of the protein A blended is preferably an amount corresponding to at least 10.0 mg/mL-bed, more preferably at least 11.5 mg/mL-bed per packing volume.

Further, in order to deactivate the epoxy groups remaining in the linker structure, after the ligand is bonded to the silica spheres, reaction with an ethanolamine or tris, or treatment with an acidic aqueous solution is preferably carried out.

The postprocessing after the reaction is not particularly limited and may be carried out by a conventional method such as filtration or washing.

Further, the carrier having the ligand immobilized is preferably refrigerated at from 4 to 8° C. at a pH of from 5 to 6, and further, benzyl alcohol or the like may be added as a preservative.

The reaction is preferably carried out so that the amount of the protein A immobilized is at least 10 mg/mL-bed, more preferably at least 11.5 mg/mL-bed, as the amount of the protein A per packing volume (the amount obtained by dividing the amount of the protein A immobilized by the packing volume).

The amount of the protein A immobilized may be obtained by a known method. For example, the amount of the protein A immobilized to the silica spheres can be calculated from the difference between the concentration of the protein A solution blended, and the concentration of the protein A solution obtained by mixing the above solution with the silica spheres to bond the protein A and then separating the silica spheres. The solution concentration may optically be measured.

In a case where the above-mentioned affinity carrier is used for chromatography, the affinity carrier is packed in a column. As the column, a column made of glass, stainless steel, a resin or the like may properly be used.

EXAMPLES

Now, the present invention will be described in further detail with reference to Examples. However, the present invention is by no means restricted to such specific Examples. In the following, the same compound is used for components in common. Further, as components not particularly described, compounds manufactured by KANTO CHEMICAL CO., INC. were used.

Preparation Example 1

Preparation of Affinity Carrier in Examples (1) Preparation of Dispersed Phase and Continuous Phase As a dispersed phase, No. 3 sodium silicate (manufactured by AGC Si-Tech Co., Ltd.) was diluted with water to prepare a sodium silicate solution having a $SiO_2$ concentration of 16.9 mass %, a $Na_2O$ concentration of 6.13 mass % ($SiO_2/Na_2O$ molar ratio=2.85) and a specific gravity of 1.222.

As a continuous phase, a solution having 1.0 mass % sorbitan monooleate (manufactured by Sanyo Chemical Industries, Ltd.) as a surfactant dissolved in linear saturated hydrocarbon decane ($C_{10}H_{22}$, manufactured by Tosoh Corporation) having a specific gravity of 0.73 was prepared.

(2) Preparation of Emulsification Apparatus

An emulsification apparatus used to emulsify the dispersed phase and the continuous phase is shown in FIG. 1.

In the emulsification apparatus shown in FIG. 1, reference symbols 1 and 2 represent a member made of an acrylic resin, 3 a stainless steel plate having a flow path (microchannel) 3a formed by etching treatment, and 4 a stainless steel plate having a plurality of micropores 4a formed. The continuous phase flows in a laminar flow state in the flow path 3a so that it is supplied from a continuous phase supply port 5 and discharged from a continuous phase discharge port 6, and the dispersed phase of the sodium silicate solution is supplied from a dispersed phase supply port 7 and injected into the continuous phase via the micropores 4a.

The stainless steel plate 3 was processed to have two flow paths 3a arranged in parallel by etching. Each of the two flow paths 3a has a size of 3.0 mm (width)×0.15 mm (thickness)× 63 mm (length).

The stainless steel plate 4 was processed by laser processing to have 26 crosswise×510 lengthwise=13,260 in total of the micropores 4a of 14 μm as a diameter of each pore as observed from a plane on the discharge port side, per flow path 3a. The surface of the stainless steel plate 4 was coated with a solvent-soluble fluororesin (CYTOP CTL-102AE manufactured by Asahi Glass Company, Limited) to impart water repellency.

(3) Preparation of Silica Spheres after Emulsification

The emulsification apparatus prepared in the above (2) was horizontally placed, the continuous phase prepared in the above (1) was supplied from the continuous phase supply port 5, and the dispersed phase of the sodium silicate solution prepared in the above (1) was supplied from the dispersed phase supply port 7 via the micropores 4a, to continuously produce a W/O emulsion having the sodium silicate solution dispersed in the continuous phase. On that occasion, the amount of supply of the continuous phase was 642 mL/h per flow path 3a, and the flow rate in a direction of flow in the flow path was 3 m/s. The experiment was carried out at room temperature, and the amount of supply of the dispersed phase was 10.4 μL/h per micropore 4a.

Then, a carbon dioxide gas was supplied for 15 minutes while the obtained emulsion was stirred to precipitate silica spheres. Further, water was added, the silica spheres were separated from the continuous phase, 20 mass % sulfuric acid was added, and $CO_2$ was removed, followed by washing with water and drying to obtain silica spheres after emulsification.

Physical properties of the obtained silica spheres after emulsification are as follows, and the silica spheres after emulsification have homogeneous particle sizes.

Average particle size: 40.6 μm
Uniformity coefficient (D90/D10): 1.31
Average pore size: 15.6 nm
Pore volume: 1.16 mL/g
Specific surface area: 298 $m^2/g$ As a measurement method, the average particle size was measured by a laser light scattering method using LA-950V2 (manufactured by Horiba, Ltd.). Further, the uniformity coefficient was obtained from the ratio (D90/D10) of the D10 particle size and the D90 particle size measured by a Coulter counter method using Multisizer III (manufactured by Beckman Coulter, Inc.).

Further, the average pore size, the pore volume and the specific surface area were measured by a mercury intrusion technique using Autopore IV9510 (manufactured by Shimadzu Corporation). The same applies hereinafter.

(4) Preparation of Silica Spheres

To 34.5 g of the silica spheres after emulsification obtained by the above emulsification step, a 1.5 mass % sodium chloride (NaCl) aqueous solution was added in an amount corresponding to 0.7 mass % to $SiO_2$, and the mixture was dried at 180° C. overnight. The mixture was put in a crucible, held at 180° C. for 6.5 hours and fired at 730° C. for 13 hours. To remove excess sodium content, the fired product was subjected to reflux with a 18% hydrochloric acid aqueous solution for 2 hours. After filtration and washing, the fired product was dipped in a predetermined amount of 0.85 M sodium hydroxide (NaOH) aqueous solution at 25° C. for 24 hours. After filtration, the fired product was washed with a sulfuric acid aqueous solution having a pH of 1.5 to obtained a final product of silica spheres.

The physical properties of the obtained silica spheres are as follows.

Average particle size: 34.4 μm
Uniformity coefficient (D90/D10): 1.31
Average pore size: 105.0 nm
Pore volume: 1.64 mL/g
Specific surface area: 60 $m^2/g$ (5) Introduction of Linker To 10 g of the obtained silica spheres, 80 mL of toluene, 4.62 mL of diisopropylethylamine and 6.00 mL of γ-glycidoxypropyl trimethoxysilane were added, followed by reflux for 4.5 hours. After air-cooling, the mixture was subjected to filtration, washed with 200 mL of toluene, 100 mL of tetrahydrofuran (THF) and 130 mL of methanol, and dried at 70° C.

The amount of the linker modified per 1 g of the obtained silica spheres was obtained by elemental analysis using a full automatic elemental analysis apparatus (CHNS/O) 2400II (manufactured by PerkinElmer Co., Ltd.), and the result was as follows.

Amount of linker modified: 260 μmol/g (6) Introduction of Ligand

To 4 g of the obtained silica spheres having the linker introduced, a 0.2M hydrogencarbonate buffer solution and recombinant protein A (prepared by a method disclosed in U.S. Pat. No. 5,084,559) in an amount corresponding to 12 mg/mL-bed per packing volume were added, followed by stirring at room temperature for 3 hours. After the mixture was subjected to filtration and washed with water, it was dipped in 16 mL of a 0.5 mass % hydrochloric acid aqueous solution at room temperature overnight to deactivate remaining epoxy groups. After filtration, the silica spheres were washed with 130 mL of a phosphate buffered saline (PBS, pH: 7.4), 130 mL of a citrate buffer solution (pH: 2.2), 130 mL of PBS again, 60 mL of a 50 mM NaOH aqueous solution and 130 mL of distilled water. The silica spheres were refrigerated in a 0.1 M acetate buffer solution (pH: 5.2) containing 1% benzyl alcohol.

The obtained affinity carrier was dried, and the amount of the protein A ligand immobilized was obtained by elemental analysis using a full automatic element analysis apparatus (CHNS/O) 2400II (manufactured by PerkinElmer Co., Ltd.), and the result was as follows per packing volume.

Amount of ligand immobilized: 11.5 mg/mL-bed

Further, the static binding capacity (SBC) was as follows. A polyclonal human IgG solution (manufactured by Sigma- Aldrich) at an initial concentration of from 0 to 1.82 mg/mL was added to the carrier having the protein A immobilized of 0.1 mL-bed, the mixture was stirred by a rotary mixer at room temperature overnight and subjected to centrifugal separation, and the 280 nm absorbance of the supernatant fluid was measured (UV-1800 (manufactured by Shimadzu Corporation)) to determine the remaining IgG concentration, and the static binding capacity was calculated by a Langmuir plot method.

Static binding capacity (SBC): 88 mg/mL-bed

Preparation Example 2

Preparation of Affinity Carrier in Comparative Examples

An affinity carrier was prepared in the same manner as in the above preparation of affinity carrier in Examples in Preparation Example 1 except that "M.S.GEL.SIL D-50-1000AW" manufactured by AGC Si-Tech Co., Ltd. was used as a final product of the silica spheres.

Physical properties of the silica spheres "M.S.GEL.SIL D-50-1000AW" used were as follows.
Average particle size: 45.7 μm
Uniformity coefficient (D90/D10): 1.93
Average pore size: 99.0 nm
Pore volume: 1.78 mL/g
Specific surface area: 71 m²/g Further, physical properties of the affinity carrier were as follows.
Amount of ligand immobilized: 11.6 mg/mL-bed
Static binding capacity (SBC): 74 mg/mL-bed Example 1

In Example 1, the affinity carrier prepared in the above Preparation Example 1 was packed in a glass column having an inner diameter of 5 mm and a length of 200 mm, to prepare a column for affinity chromatography.

Comparative Examples 1 to 3

In Comparative Example 1, a column for affinity chromatography was prepared in the same manner as in Example 1 except that the affinity carrier in Comparative Examples prepared in Preparation Example 2 was used.

In Comparative Example 2, a column for affinity chromatography was prepared in the same manner as in Example 1 except that a commercially available agarose carrier (Mab-Select SuRe, manufactured by GE Healthcare) was used.

In Comparative Example 3, a column for affinity chromatography was prepared in the same manner as in Example 1 except that a commercially available CPG (controlled pore glass) carrier (Prosep Ultra Plus, manufactured by Millipore) was used.

<Evaluation>

The relation between the linear flow rate and the pressure loss when water was made to pass through each of the columns in Example 1 and Comparative Examples 1 to 3 was measured. The results are shown in FIG. 2.

The affinity carrier was packed in a glass column having an inner diameter of 5 mm and a length of 200 mm, the column was set to a chromatography apparatus "AKTA explorer 10S" (manufactured by GE Healthcare), and distilled water was made to pass at each linear flow rate to obtain the operating pressure A. Then, the operating pressure B was obtained in the same manner except that the affinity carrier was not packed in the column. The operating pressure B was subtracted from the operating pressure A at each linear flow rate to determine the pressure low.

Figure 2:
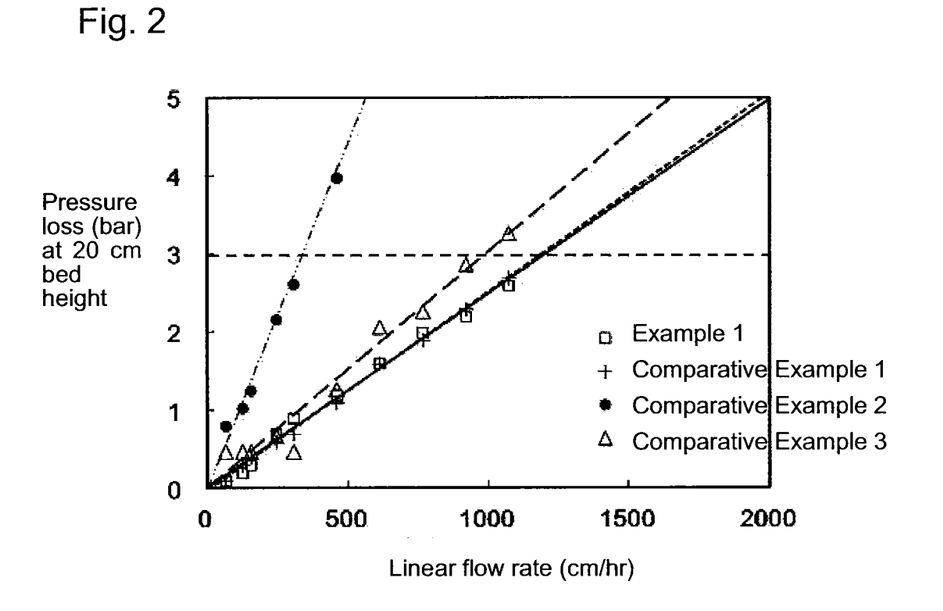
FIG. 2 is a graph illustrating the relation between the linear flow rate and the pressure low of a column in each of Example and Comparative Examples.

As shown in FIG. 2, the pressure losses in Example 1 (the approximate straight line indicated by a solid line) and Comparative Example 1 (the approximate straight line indicated by a dotted line) were equal to each other and were so low as at most 3 bar at a high linear flow rate of 1,200 cm/hr corresponding to a residence time of 1 minute. Although the silica spheres in Example 1 had a smaller average particle size than in Comparative Example 1, as their uniformity coefficient is low, the pressure loss can be suppressed low. On the other hand, in Comparative Example 2 (the approximate linear line indicated by a two-dot chain line) in which the agarose carrier was used, the pressure loss was so high as least 10 bar at the same linear flow rate, and in Comparative Example 3 (the approximate straight line indicated by a broken line) in which the CPG carrier was used, the pressure loss was at least 3 bar at the same linear flow rate.

Example 2

In Example 2, the affinity carrier prepared in Preparation Example 1 was packed in a glass column having an inner diameter of 5 mm and a length of 50 mm to prepare a column for affinity chromatography.

Comparative Examples 4 to 8

In Comparative Example 4, a column for affinity chromatography was prepared in the same manner as in Example 2 except that the affinity carrier prepared in Preparation Example 2 was used.

In Comparative Example 5, a column for affinity chromatography was prepared in the same manner as in Example 2 except that a commercially available agarose carrier (Mab-Select Xtra, manufactured by GE Healthcare) was used.

In Comparative Example 6, a column for affinity chromatography was prepared in the same manner as in Example 2 except that a commercially available agarose carrier (Mab-Select SuRe, manufactured by GE Healthcare) was used.

In Comparative Example 7, a column for affinity chromatography was prepared in the same manner as in Example 2 except that a commercially available agarose carrier (Mab-Select SuRe XL, manufactured by GE Healthcare) was used.

In Comparative Example 8, a column for affinity chromatography was prepared in the same manner as in Example 2 except that a commercially available CPG (controlled pore glass) carrier (Prosep Ultra Plus, manufactured by Millipore) was used.

<Evaluation>

Figure 3:
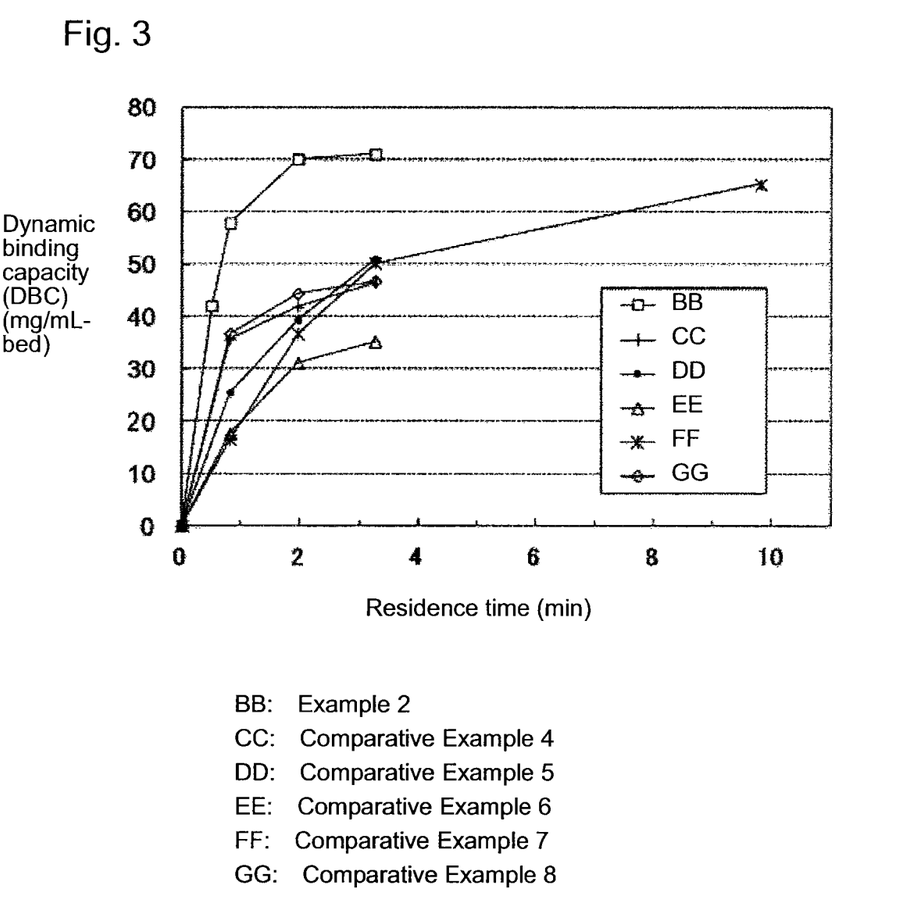
FIG. 3 is a graph illustrating the relation between the residence time and the dynamic binding capacity of a column in each of Example and Comparative Examples.

The dynamic binding capacity (DBC) was measured by the following procedure, and the results are shown in FIG. 3. Each of the column in Example 2 and Comparative Example 5 to 8 was set to a chromatography apparatus "AKTA explorer 10S" (manufactured by GE Healthcare), and PBS (pH: 7.4) containing 0.5 mg/mL polyclonal human IgG was made to pass through each column at various linear flow rates. At the time when 10% breakthrough of the absorbance of the eluate was measured to the absorbance of the PBS (pH: 7.4) containing 0.5 mg/mL polyclonal human IgG which was made to pass, the mass of the added polyclonal human IgG was obtained to calculate the dynamic binding capacity.

As shown in FIG. 3, with the column in Example 2, a large dynamic binding capacity was obtained as compared with Comparative Examples 4 to 8. In a high linear flow rate region corresponding to a residence time of 1 minute, in Comparative Examples 5 to 7 in which the agarose carrier was used, the dynamic binding capacity was from 20 to 30 mg/mL-bed, and in Comparative Example 8 in which the CPG carrier was used and in Comparative Example 4 in which the column in Preparation Example 2 was used, it was about 40 mg/mL-bed, whereas the column in Example 2 had a high performance with the dynamic binding capacity of about 60 mg/mL-bed.

INDUSTRIAL APPLICABILITY

The silica spheres of the present invention are applicable to preparation of an affinity carrier having a ligand immobilized to the silica spheres and having a large binding capacity.

This application is a continuation of PCT Application No. PCT/JP2012/077788, filed on Oct. 26, 2012, which is based upon and claims the benefit of priority from Japanese Patent Application No. 2011-237204 filed on Oct. 28, 2011. The contents of those applications are incorporated herein by reference in their entireties.

REFERENCE SYMBOLS

1: Plate made of acrylic resin
2: Plate made of acrylic resin
3: Stainless steel plate
3a: Flow path
4: Stainless steel plate
4a: Micropore
5: Continuous phase supply port
6: Continuous phase discharge port
7: Dispersed phase supply port

What is claimed is:

1. Spheres consisting of silica, wherein:
(a) an average particle size of the silica spheres is from 30 μm to 40 μm as measured by a laser light scattering method;
(b) in a particle size distribution of the silica spheres as measured by a Coulter counter method a ratio of the average particle size (D90) of the 90% cumulative volume of the silica spheres to the particle size (D10) of the smallest 10% cumulative volume (D90/D10) is at most 1.50;
(c) an average pore size of the silica spheres is from 85 nm to 115 nm; and
(d) a pore volume of the silica spheres is at least 1.5 mL/g, as measured by a mercury intrusion technique.

2. The silica spheres according to claim 1, wherein the ratio of D90/D10 is at most 1.35.

3. The silica spheres according to claim 1, wherein the average particle size is from 33 μm to 37 μm.

4. The silica spheres according to claim 1, wherein a specific surface area of the silica spheres is from 55 $m^2/g$ to 75 $m^2/g$.

5. An affinity carrier comprising the silica spheres of claim 1, wherein a ligand is immobilized to the silica spheres.

6. The affinity carrier according to claim 5, wherein the ligand is protein A, and an amount of the protein A immobilized is at least 10 mg/mL-bed.

7. The affinity carrier according to claim 5, wherein a dynamic binding capacity of the affinity carrier is at least 50 mg/mL-bed.

8. A method to prepare the silica spheres of claim 1, comprising:
emulsifying an aqueous solution of an alkali metal silicate in an organic liquid to form a W/O emulsion having uniform aqueous metal silicate droplets in the organic liquid,
adding a gelling agent to the emulsion to obtain spherical hydrogel aqueous phase,
separating the aqueous phase comprising a slurry of the spherical hydrogel from the organic liquid phase,
adjusting the pH of the aqueous slurry of the silica hydrogel to from 1 to 5 to complete gelation,
filtering the spherical hydrogel from the aqueous slurry, and
drying the spherical hydrogel to obtain the silica spheres.

9. The method of claim 8, wherein the alkali metal of the alkali metal silicate is at least one selected from the group consisting of lithium, sodium, potassium and rubidium.

10. The method of claim 8, wherein the alkali metal of the alkali metal silicate is sodium.

11. The method of claim 8, wherein a molar ratio of silicic acid to sodium calculated as sodium oxide ($SiO_2/Na_2O$) in the aqueous solution of the alkali metal silicate is from 2.0 to 3.8.

12. The method of claim 8, wherein a concentration of the alkali metal silicate calculated as $SiO_2$ in the aqueous solution of the alkali metal silicate is from 5 to 30 mass %.

13. The method of claim 8, wherein the emulsion comprises supplying the aqueous solution of the alkali metal silicate to the organic liquid through micropores or a porous membrane.

* * * * *